US012633373B2

(12) United States Patent
Dror et al.

(10) Patent No.: US 12,633,373 B2
(45) Date of Patent: May 19, 2026

(54) SYSTEMS AND METHODS TO PREDICT STRUCTURES AND PROPERTIES OF BIOMOLECULE-LIGAND COMPLEXES AND USES THEREOF

(71) Applicant: The Board of Trustees of the Leland Stanford Junior University, Stanford, CA (US)

(72) Inventors: Ron O. Dror, Stanford, CA (US); Joseph M. Paggi, Stanford, CA (US)

(73) Assignee: The Board of Trustees of the Leland Stanford Junior University, Stanford, CA (US)

(*) Notice: Subject to any disclaimer, the term of this patent is extended or adjusted under 35 U.S.C. 154(b) by 700 days.

(21) Appl. No.: 18/000,264

(22) PCT Filed: May 27, 2021

(86) PCT No.: PCT/US2021/034637
§ 371 (c)(1),
(2) Date: Nov. 29, 2022

(87) PCT Pub. No.: WO2021/243097
PCT Pub. Date: Dec. 2, 2021

(65) Prior Publication Data
US 2023/0245713 A1      Aug. 3, 2023

Related U.S. Application Data

(60) Provisional application No. 63/031,957, filed on May 29, 2020.

(51) Int. Cl.
G16B 15/30        (2019.01)
G06N 5/022        (2023.01)
G16B 40/20        (2019.01)

(52) U.S. Cl.
CPC ............ *G16B 15/30* (2019.02); *G06N 5/022* (2013.01); *G16B 40/20* (2019.02)

(58) Field of Classification Search
CPC ......... G16B 15/30; G16B 40/20; G06N 5/022
See application file for complete search history.

(56) References Cited

U.S. PATENT DOCUMENTS 8,150,634 B1 *    4/2012    Constantine ........... G16B 15/30
                                                          703/11
11,450,407 B1 *    9/2022    Laniado ................ G16B 15/30
                          (Continued)

FOREIGN PATENT DOCUMENTS

WO        2021243097 A1    12/2021

OTHER PUBLICATIONS

International Preliminary Report on Patentability for International Application No. PCT/US2021/034637, Report issued Nov. 17, 2022, Mailed on Dec. 8, 2022, 7 pgs.
(Continued)

*Primary Examiner* — Eliyah S. Harper
(74) *Attorney, Agent, or Firm* — KPPB LLP

(57)        ABSTRACT

Embodiments herein describe systems and methods to predict biomolecule-ligand complexes and uses thereof. Many embodiments generate candidate poses and docking scores for ligands known to interact with a target protein as well as a candidate ligand. Based on similarities present in the candidate poses and docking scores, a pose for the candidate ligand is identified. Many embodiments determine whether a candidate ligand can bind to a target and, if so, determine an affinity. Many embodiments can be used for virtual screening or lead optimization.

18 Claims, 8 Drawing Sheets

Distinct ligands tend to form similar interactions with the target

(56) References Cited

U.S. PATENT DOCUMENTS

| | | | | | |
|---|---|---|---|---|---|
| 12,027,235 | B1 * | 7/2024 | El Hibouri | .............. | G16B 40/20 |
| 12,367,329 | B1 * | 7/2025 | Candido | .................. | G06F 30/27 |
| 12,368,503 | B2 * | 7/2025 | Prasad | ............... | H04B 7/18532 |
| 2010/0112724 | A1 | 5/2010 | Tovbin et al. | | |
| 2011/0112818 | A1 | 5/2011 | Goddard, III et al. | | |
| 2018/0141958 | A1 * | 5/2018 | Morikis | ............... | A61K 31/165 |
| 2019/0369097 | A1 | 12/2019 | Fiser et al. | | |
| 2020/0143911 | A1 * | 5/2020 | Juraszek | ................. | G16C 20/30 |
| 2023/0034425 | A1 * | 2/2023 | Laniado | .................. | G16B 40/20 |
| 2023/0245713 | A1 * | 8/2023 | Dror | ...................... | G16B 40/20 |
| | | | | | 706/46 |

OTHER PUBLICATIONS

International Search Report and Written Opinion for International Application No. PCT/US2021/034637, Search completed Aug. 25, 2021, Mailed Sep. 30, 2021, 14 pgs.

Allen et al., "DOCK 6: Impact of New Features and Current Docking Performance", Journal of Computational Chemistry, vol. 36, No. 15, Jun. 5, 2015, pp. 1132-1156, doi: 10.1002/jcc.23905.

Bajusz et al., "Why is Tanimoto index an appropriate choice for fingerprint-based similarity calculations?", Journal of Cheminformatics, vol. 7, No. 20, May 20, 2015, pp. 1-13, doi: 10.1186/s13321-015-0069-3.

Bissantz et al., "A Medicinal Chemist's Guide to Molecular Interactions", Journal of Medicinal Chemistry, vol. 53, No. 14, Mar. 26, 2010, pp. 5061-5084, doi: 10.1021/jm100112j.

Cherkasov et al., "QSAR modeling: where have you been? Where are you going to?", Journal of Medicinal Chemistry, vol. 57, No. 12, Dec. 18, 2013, pp. 4977-5010, doi: 10.1021/jm4004285.

Chupakhin et al., "Predicting ligand binding modes from neural networks trained on protein-ligand interaction fingerprints", Journal of Chemical Information and Modeling, vol. 53, No. 4, Mar. 12, 2013, pp. 763-772, doi: 10.1021/ci300200r.

Cleves et al., "Electrostatic-field and surface-shape similarity for virtual screening and pose prediction", Journal of Computer-Aided Molecular Design, vol. 33, 2019, [online] [retrieved on Aug. 24, 2021] Retrieved from the Internet https://link.springer.com/article/10.1007/s10822-019-00236-6 >, entire document, pp. 865-886, doi: 10.1007/s10822-019-00236-6.

Cleves et al., "Quantitative surface field analysis: learning causal models to predict ligand binding affinity and pose", Journal of Computer-Aided Molecular Design, vol. 32, 2018, pp. 731-757, doi: 10.1007/s10822-018-0126-x.

Cramer et al., "Comparative Molecular Field analysis (CoMFA). 1. Effect of Shape on Binding of Steroids to Carrier Proteins", Journal of American Chemical Society, vol. 110, No. 18, Aug. 1, 1988, pp. 5959-5967, doi: 10.1021/ja00226a005.

Da et al., "Structural Protein-Ligand Interaction Fingerprints (SPLIF) for Structure-Based Virtual Screening: Method and Benchmark Study", Journal of Chemical Information and Modeling, vol. 54, No. 9, Aug. 13, 2014, pp. 2555-2561, doi: 10.1021/cI500319f.

Das et al., "Automated de novo prediction of native-like RNA tertiary structures", PNAS, vol. 104, No. 37, Sep. 11, 2007, pp. 14664-14669, doi: 10.1073/pnas.0703836104.

Fan et al., "Haloperidol bound D(2) dopamine receptor structure inspired the discovery of subtype selective ligands", Nature Communications, vol. 11, No. 1, Article 1074, Feb. 26, 2020, 11 pgs., doi: 10.1038/s41467-020-14884-y.

Friesner et al., "Extra precision glide: docking and scoring incorporating a model of hydrophobic enclosure for protein-ligand complexes", Journal of Medicinal Chemistry, vol. 49, No. 21, Sep. 23, 2006, pp. 6177-6196, doi: 10.1021/jm0512560.

Friesner et al., "Glide: A New Approach for Rapid, Accurate Docking and Scoring. 1. Method and Assessment of Docking Accuracy", Journal of Medicinal Chemistry, vol. 47, No. 7, Feb. 27, 2004, pp. 1739-1749, doi: 10.1021/jm0306430.

Fu et al., "RosettaLigandEnsemble: A Small-Molecule Ensemble-Driven Docking Approach", ACS Omega, vol. 3, No. 4, Apr. 2, 2018, pp. 3655-3664 doi: 10.1021/acsomega.7b02059.

Gainza et al., "Deciphering interaction fingerprints from protein molecular surfaces using geometric deep learning", Nature Methods, vol. 17, No. 2, Feb. 2020, published online Dec. 9, 2019, pp. 184-192, doi: 10.1038/s41592-019-0666-6.

Gaulton et al., "The ChEMBL database in 2017", Nucleic Acids Research, vol. 45, No. D1, Jan. 2017, pp. D945-D954, doi: 10.1093/nar/gkw1074.

Hand et al., "Idiot's Bayes: Not So Stupid after All?", International Statistical Review/ Revue Internationale de Statistique, vol. 69, No. 3, Dec. 2001, pp. 385-398, doi: 10.2307/1403452.

Hauser et al., "Pharmacogenomics of GPCR Drug Targets", Cell, vol. 172, No. 1-2, Jan. 11, 2018, pp. 41-54.e19, Open Access published Dec. 14, 2017, doi: 10.1016/j.cell.2017.11.033.

Jain, "Surflex: Fully Automatic Flexible Molecular Docking Using a Molecular Similarity-Based Search Engine", Journal of Medicinal Chemistry, vol. 46, No. 4, Jan. 21, 2003, pp. 499-511, 10.1021/jm020406h.

Jones et al., "Development and Validation of a Genetic Algorithm for Flexible Docking", Journal of Molecular Biology, vol. 267, No. 3, Apr. 4, 1997, pp. 727-748, doi: 10.1006/jmbi.1996.0897.

Kramer et al., "The Experimental Uncertainty of Heterogeneous Public Ki Data", Journal of Medicinal Chemistry, vol. 55, No. 11, May 29, 2012, pp. 5165-5173, doi: 10.1021/jm300131x.

Kuntz et al., "A Geometric Approach to Macromolecule-Ligand Interactions", Journal of molecular biology, vol. 161, No. 2, Oct. 25, 1982, pp. 269-288, doi: 10.1016/0022-2836(82)90153-X.

Leelananda et al., "Computational methods in drug discovery", Beilstein Journal of Organic Chemistry, vol. 12, Dec. 12, 2016, pp. 2694-2718, doi: 10.3762/bjoc.12.267.

Lim et al., "Predicting Drug-Target Interaction Using a Novel Graph Neural Network with 3D Structure-Embedded Graph Representation", Journal of Chemical Information and Modeling, vol. 59, No. 9, Aug. 23, 2019, published online Sep. 6, 2019, pp. 3981-3988, doi: 10.1021/acs.jcim.9b00387.

Malhotra et al., "When Does Chemical Elaboration Induce a Ligand To Change Its Binding Mode?", Journal of Medicinal Chemistry, vol. 60, Jan. 12, 2017, pp. 128-145, published online Dec. 16, 2016, doi: 10.1021/acs.jmedchem.6b00725.

Pagadala et al., "Software for molecular docking: a review", Biophys Review, vol. 9, No. 2, Apr. 2017, pp. 91-102, published online Jan. 16, 2017, doi: 10.1007/s12551-016-0247-1.

Platzer et al., "Conformational Energy Calculations of Enzyme-Substrate Interactions. II. Computation of the Binding Energy for Substrates in the Active Site of α-Chymotrypsin", International Journal of Peptide and Protein Research, vol. 4, No. 3, May 1972, pp. 201-219, doi: 10.1111/j.1399-3011.1972.tb03420.x.

Ragoza et al., "Protein-Ligand Scoring with Convolutional Neural Networks", Journal of Chemical Information and Modeling, vol. 57, No. 4, Apr. 24, 2017, pp. 942-957, doi: 10.1021/acs.jcim.6b00740.

Rarey et al., "A Fast Flexible Docking Method using an Incremental Construction Algorithm", Journal of Molecular Biology, vol. 261, No. 3, Aug. 23, 1996, pp. 470-489, doi: 10.1006/jmbi.1996.0477.

Renner et al., "Maximum Common Binding Modes (MCBM): Consensus Docking Scoring Using Multiple Ligand Information and Interaction Fingerprints", Journal of Chemical Information and Modeling, vol. 48, No. 2, published on web Jan. 23, 2008, pp. 319-332, doi: 10.1021/ci7003626.

Santos et al., "A comprehensive map of molecular drug targets", Nature Review Drug Discovery, vol. 16, No. 1, Jan. 2017, published online Dec. 2, 2016, pp. 19-34, doi: 10.1038/nrd.2016.230.

Sastry et al., "Rapid Shape-Based Ligand Alignment and Virtual Screening Method Based on Atom/Feature-Pair Similarities and vol. Overlap Scoring", Journal of Chemical Information and Modeling, vol. 51, No. 10, Aug. 28, 2011, published online Sep. 15, 2011, pp. 2455-2466, doi: 10.1021/ci2002704.

Sherman et al., "Novel Procedure for Modeling Ligand/Receptor Induced Fit Effects", Journal of Medicinal Chemistry, vol. 49, No. 2, Dec. 23, 2005, pp. 534-553, doi: 10.1021/jm050540c.

Sippl, "Boltzmann's principle, knowledge-based mean fields and protein folding. An approach to the computational determination of

(56)　　　　　References Cited

OTHER PUBLICATIONS protein structures", Journal of Computer-Aided Molecular Design, vol. 7, Aug. 1993, pp. 473-501, doi: 10.1007/BF02337562.

Sippl, "Calculation of Conformational Ensembles from Potentials of Mean Force. An Approach to the Knowledge-based Prediction of Local Structures in Globular Proteins", Journal of Molecular Biology, vol. 213, No. 4, Jun. 20, 1990, pp. 859-883, doi: 10.1016/S0022-2836(05)80269-4.

Sliwoski et al., "Computational Methods in Drug Discovery", Pharmacological Reviews, vol. 66, No. 1, Jan. 2014, pp. 334-395, doi: 10.1124/pr.112.007336.

Trott et al., "AutoDock Vina: improving the speed and accuracy of docking with a new scoring function, efficient optimization, and multithreading", Journal of Computational Chemistry, vol. 31, No. 2, Jan. 30, 2010, pp. 455-461, doi: 10.1002/jcc.21334.

Venkatachalam et al., "LigandFit: a novel method for the shape-directed rapid docking of ligands to protein active sites", Journal of Molecular Graphics and Modelling, vol. 21, No. 4, Jan. 2003, pp. 289-307, doi: 10.1016/S1093-3263(02)00164-X.

Verma et al., "3D-QSAR in Drug Design—a Review", Current Topics in Medicinal Chemistry, vol. 10, No. 1, 2010, pp. 95-115, doi: 10.2174/156802610790232260.

Vieth et al., "DOMCoSAR: A Novel Approach for Establishing the Docking Mode That is Consistent With the Structure-Activity Relationship. Application to HIV-1 Protease Inhibitors and VEGF Receptor Tyrosine Kinase Inhibitors", Journal of Medicinal Chemistry, vol. 43, No. 16, Jul. 21, 2000, pp. 3020-3032, doi: 10.1021/jm990609e.

Wallach et al., "Predicting Multiple Ligand Binding Modes Using Self-Consistent Pharmacophore Hypotheses", Journal of Chemical Information and Modeling, vol. 49, No. 9, Aug. 27, 2009, pp. 2116-2128, doi: 10.1021/ci900199e.

Wang et al., "Comprehensive evaluation of ten docking programs on a diverse set of protein-ligand complexes: the prediction accuracy of sampling power and scoring power", Physical Chemistry Chemical Physics, vol. 18, 2016, pp. 12964-12975, doi: 10.1039/C6CP01555G.

Wang et al., "Structure of the D2 dopamine receptor bound to the atypical antipsychotic drug risperidone", Nature, vol. 555, No. 7695, Mar. 8, 2018, published online Jan. 24, 2018, pp. 269-273, doi: 10.1038/nature25758.

Wang et al., "The PDBbind Database: Methodologies and Updates", Journal Medicinal Chemistry, vol. 48, No. 12, May 24, 2005, pp. 4111-4119, doi: 10.1021/jm048957q.

Yu et al., "Computer-Aided Drug Design Methods", Antibiotics, Methods in Molecular Biology, vol. 1520, Chapter 5, Humana Press, Nov. 22, 2016, pp. 85-106, doi: 10.1007/978-1-4939-6634-9_5.

Alam et al., "3D-QSAR, Docking, ADME/Tox studies on Flavone analogs reveal anticancer activity through Tankyrase inhibition", Scientific Reports, vol. 9, Article 5414, Apr. 1, 2019, 15 pgs., doi: 10.1038/s41598-019-41984-7.

Li et al., "An Overview of Scoring Functions Used for Protein—Ligand Interactions in Molecular Docking", Interdisciplinary Sciences: Computational Life Sciences, vol. 11, Jun. 1, 2019, pp. 320-328, doi: 10.1007/s12539-019-00327-w.

Papadatos et al., "Activity, assay and target data curation and quality in the ChEMBL database", Journal of Computer-Aided Molecular Design, vol. 29, Jul. 23, 2015, pp. 885-896, doi: 10.1007/s10822-015-9860-5.

* cited by examiner

Distinct ligands tend to form similar interactions with the target

Identify target protein and query ligand — 302

Obtain a set of helper ligands — 304

Predict initial binding poses — 306

Quantify similarities of binding poses — 308

300

Per-ligand docking underestimates the structural similarity of distinct ligands' binding poses $$\text{Interaction Similarity} = \frac{1 + \text{number of shared interactions}}{2 + \text{total number of unique interactions}}$$

Obtain target protein structure — 702

Obtain a set of helper ligands — 704

Identify a pose for each helper ligand — 706

Obtain a set of query molecules — 708

Identify binding affinity for a query molecule — 710

Identify a modifiable position — 712

Alter the modifiable position — 714

Determine a new binding affinity — 716

700

SYSTEMS AND METHODS TO PREDICT STRUCTURES AND PROPERTIES OF BIOMOLECULE-LIGAND COMPLEXES AND USES THEREOF

CROSS-REFERENCE TO RELATED APPLICATIONS

The current application is a national stage of PCT Patent Application No. PCT/US2021/034637 entitled "Systems and Methods to Predict Structures and Properties of Bio-molecule-Ligand Complexes and Uses Thereof" filed May 27, 2021, which claims priority to U.S. Provisional Patent Application No. 63/031,957 entitled "Systems and Methods to Predict Protein-Ligand Complexes and Uses Thereof" filed May 29, 2020, the disclosures of which are hereby incorporated by reference in their entireties.

FIELD OF THE INVENTION

The present invention relates to biomolecule-ligand inter-actions. More specifically, the present invention relates to a methods and systems to predict biomolecule-ligand com-plexes showing higher accuracy in determining pose and/or binding affinity.

BACKGROUND

Binding of small-molecule ligands to proteins is one of the most fundamental processes in biology, and the great majority of drugs are ligands that exert their effects by binding to a target protein. Predicting properties of protein-ligand interactions—including three-dimensional (3D) structures, binding affinities, binding kinetics, selectivity, and functional effects—is critical both to the rational design of effective medicines and to solving major problems in molecular biology. An enormous amount of work has thus focused on the development of computational methods to predict these properties. (See e.g., W. Yu, A. D. MacKerell, Jr., Computer-Aided Drug Design Methods. Methods Mol Biol 1520, 85-106 (2017); and G. Sliwoski, S. Kothiwale, J. Meiler, E. W. Lowe, Jr., Computational methods in drug discovery. Pharmacol Rev 66, 334-395 (2013); the disclo-sures of which are incorporated herein by reference in their entireties.)

Such computational methods generally fall into two cat-egories. "Physics-based" approaches use a 3D structure of the target protein and exploit an understanding of the physics of protein-ligand interactions. (See e.g., J. Li, A. Fu, L. Zhang, An Overview of Scoring Functions Used for Protein-Ligand Interactions in Molecular Docking. Interdiscip Sci 11, 320-328 (2019); the disclosure of which is incorporated herein by reference in its entirety) "Ligand-based" approaches use experimental measurements for many ligands of a given property (e.g., affinity) at a given target and employ pattern matching to predict the corresponding property for other ligands. (See e.g., S. P. Leelananda, S. Lindert, Computational methods in drug discovery. Beilstein J Org Chem 12, 2694-2718 (2016); and A. Cherkasov et al., QSAR modeling: where have you been? Where are you going to? Journal of medicinal chemistry 57, 4977-5010 (2014); the disclosures of which are incorporated herein by reference in their entireties.) However, such methodologies generally produce inaccurate results, thus are insufficient for broad use.

SUMMARY OF THE INVENTION

This summary is meant to provide some examples and is not intended to be limiting of the scope of the invention in any way. For example, any feature included in an example of this summary is not required by the claims, unless the claims explicitly recite the features. Various features and steps as described elsewhere in this disclosure may be included in the examples summarized here, and the features and steps described here and elsewhere can be combined in a variety of ways.

In one embodiment, a method for predicting ligand-protein interaction includes obtaining a set of ligands known to bind to a target protein, generating a set of candidate poses for each ligand in the set of ligands and a candidate ligand, and determining a pose for the candidate ligand based on a similarity of the candidate poses for the candidate ligand and the candidate poses for each ligand in the set of ligands.

In a further embodiment, generating a set of candidate poses is accomplished by docking at least one ligand from the set of ligands using docking software.

In another embodiment, the method further includes gen-erating a set of scores for each ligand is using docking software.

In a still further embodiment, the docking software is selected from Glide, DOCK, AutoDock VINA, FlexX, GOLD, and Surflex.

In still another embodiment, at least one ligand in the set of ligands has an experimentally determined pose.

In a yet further embodiment, the pose for the at least one ligand is set to the experimentally determined pose.

In yet another embodiment, the similarity is based on pairwise comparisons between each ligand in the set of ligands and every other ligand in the set of ligands and pairwise comparisons between the candidate ligand and every ligand in the set of ligands.

In a further embodiment again, the similarity is further based on pairwise comparisons of substructures between each ligand in the set of ligands and every other ligand in the set of ligands and pairwise comparisons between the can-didate ligand and every ligand in the set of ligands.

In another embodiment again, the similarity is further based on pairwise comparisons of a protein-ligand interac-tion between each ligand in the set of ligands and every other ligand in the set of ligands and pairwise comparisons between the candidate ligand and every ligand in the set of ligands.

In a further additional embodiment, the protein-ligand interaction is selected from a hydrogen bond, a salt bridge, and a hydrophobic interaction.

In another additional embodiment, determining a pose for the candidate ligand includes determining a pose for each ligand in the set of ligands that minimizes the potential of all ligands.

In a still yet further embodiment, the potential is deter-mined by:

$$E(L) = (n-1)E^{dock}(L) + E^{pairwise}(L),$$

where $L=(\ell_1, \ldots, \ell_n)$ indexes the candidate poses for each ligand, n is the number of ligands, $E^{dock}$ represents the standard docking scores for the set of ligand poses, and $E^{pairwise}$ represents a pairwise contribution to the total score.

In still yet another embodiment, $E^{pairwise}(L) = \Sigma_{(i,j), i \neq j} e^{pairwise}(\ell_i, \ell_j)$.

In a still further embodiment again, $e^{pairwise}$ is determined using a machine learning algorithm.

In still another embodiment again, the machine learning algorithm is fit to a benchmark set of pairs of correct poses and pairs of incorrect poses for a diverse set of proteins.

In a still further additional embodiment, determining a pose for each ligand in the set of ligands includes utilizing an expectation-maximization algorithm.

In still another additional embodiment, the method further includes altering a pose of a ligand in the set of ligands or the candidate ligand to optimize that ligand's contribution to the potential function.

In a yet further embodiment again, a method for virtual screening includes obtaining a set of ligands known to bind to a target protein, determining a pose for each ligand in the set of ligands by generating a set of candidate poses for ligands in the set of ligands, where the pose is based on a similarity of the candidate poses for each ligand in the set of ligands, and determining a binding affinity of at least one candidate ligand by determining whether the candidate ligands binds to the target protein based on similarities to each ligand in the set of ligands and determining an energy if the candidate ligand binds to the target ligand.

In yet another embodiment again, determining a binding affinity of a candidate ligand determines a binding affinity of at least two candidate ligands.

In a yet further additional embodiment, the method further includes obtaining a library of candidate ligands, and determining a binding affinity of at least one candidate ligand determines a binding affinity of at least one candidate ligand in the library of candidate ligands.

In yet another additional embodiment, the method further includes fixing a pose for each ligand in the set of ligands prior to determining a binding affinity of at least one candidate ligand.

In a further additional embodiment again, the similarity is based on pairwise comparisons between each ligand in the set of ligands and every other ligand in the set of ligands.

In another additional embodiment again, the similarities are further based on pairwise comparisons of substructures between each ligand in the set of ligands and every other ligand in the set of ligands and pairwise comparisons between the candidate ligand and every ligand in the set of ligands.

In a still yet further embodiment again, the similarities are further based on pairwise comparisons of a protein-ligand interaction between each ligand in the set of ligands and every other ligand in the set of ligands and pairwise comparisons between the candidate ligand and every ligand in the set of ligands.

In still yet another embodiment again, the protein-ligand interaction is selected from a hydrogen bond, a salt bridge, and a hydrophobic interaction.

In a still yet further additional embodiment, determining a pose for the candidate ligand includes determining a pose for each ligand in the set of ligands that minimizes the potential of all ligands.

In still yet another additional embodiment, the potential is determined by:

$$E(L) = (n-1)E^{dock}(L) + E^{pairwise}(L),$$

where $L=(\ell_1, \ldots, \ell_n)$ indexes the candidate poses for each ligand, n is the number of ligands, $E^{dock}$ represents the standard docking scores for the set of ligand poses, and $E^{pairwise}$ represents a pairwise contribution to the total score.

In a yet further additional embodiment again, $E^{pairwise}(L)=\Sigma_{(i,j),i\neq j}e^{pairwise}(\ell_i, \ell_j)$.

In yet another additional embodiment again, $e^{pairwise}$ is determined using a machine learning algorithm.

In a still yet further additional embodiment again, the machine learning algorithm is fit to a benchmark set of pairs of correct poses and pairs of incorrect poses for a diverse set of proteins.

In still yet another additional embodiment again, determining a pose for each ligand in the set of ligands includes utilizing an expectation-maximization algorithm.

In another further embodiment, the method further includes altering a pose of a ligand in the set of ligands to optimize that ligand's contribution to the potential function.

In still another further embodiment, a method for lead optimization includes obtaining a set of ligands known to bind to a target protein, determining a pose for each ligand in the set of ligands by generating a set of candidate poses and scores for ligands in the set of ligands, where the pose is based on a similarity of the candidate poses and scores for each ligand in the set of ligands, determining a binding affinity of a candidate ligand by determining whether the candidate ligands binds to the target protein based on similarities to each ligand in the set of ligands and determining an energy if the candidate ligand binds to the target ligand, and modifying a location of the candidate ligand.

In yet another further embodiment, the method further includes identifying a modifiable location on the candidate ligand, and the modifying a location step includes modifying the modifiable location.

In another further embodiment again, modifying the location increases binding affinity of the candidate ligand.

Another further additional embodiment, the method further includes determining a binding affinity of the modified candidate ligand to the target protein based on similarities to each ligand in the set of ligands and determining an energy if the candidate ligand binds to the target ligand.

In a further embodiment, the similarity is based on pairwise comparisons between each ligand in the set of ligands and every other ligand in the set of ligands.

In another embodiment, the similarities are further based on pairwise comparisons of substructures between each ligand in the set of ligands and every other ligand in the set of ligands and pairwise comparisons between the candidate ligand and every ligand in the set of ligands.

In a still further embodiment, the similarities are further based on pairwise comparisons of a protein-ligand interaction between each ligand in the set of ligands and every other ligand in the set of ligands and pairwise comparisons between the candidate ligand and every ligand in the set of ligands.

In still another embodiment, the protein-ligand interaction is selected from a hydrogen bond, a salt bridge, and a hydrophobic interaction.

In a yet further embodiment, determining a pose for the candidate ligand includes determining a pose for each ligand in the set of ligands that minimizes the potential of all ligands.

In yet another embodiment, the potential is determined by:

$$E(L) = (n-1)E^{dock}(L) + E^{pairwise}(L),$$

where $L=(\ell_1, \ldots, \ell_n)$ indexes the candidate poses for each ligand, n is the number of ligands, $E^{dock}$ represents the standard docking scores for the set of ligand poses, and $E^{pairwise}$ represents a pairwise contribution to the total score.

In a yet further additional embodiment again, $E^{pairwise}$ (L)=$\Sigma_{(i,j),i\neq j}e^{pairwise}(\ell_i, \ell_j)$.

In another embodiment again, $e^{pairwise}$ is determined using a machine learning algorithm.

In a further additional embodiment, the machine learning algorithm is fit to a benchmark set of pairs of correct poses and pairs of incorrect poses for a diverse set of proteins.

In another additional embodiment, determining a pose for each ligand in the set of ligands includes utilizing an expectation-maximization algorithm.

In a still yet further embodiment, the method further includes altering a pose of a ligand in the set of ligands to optimize that ligand's contribution to the potential function.

In still yet another embodiment, a method for predicting ligand-biomolecule interaction includes obtaining a set of ligands known to bind to a target biomolecule, generating a set of candidate poses for each ligand in the set of ligands and a candidate ligand, and determining a pose for the candidate ligand based on a similarity of the candidate poses for the candidate ligand and the candidate poses for each ligand in the set of ligands.

In a still further embodiment again, generating a set of candidate poses is accomplished by docking at least one ligand from the set of ligands using docking software.

In still another embodiment again, the method further includes generating a set of scores for each ligand using docking software.

In a still further additional embodiment, the docking software is selected from Glide, DOCK, AutoDock VINA, FlexX, GOLD, and Surflex.

In still another additional embodiment, at least one ligand in the set of ligands has an experimentally determined pose.

In a yet further embodiment again, the pose for the at least one ligand is set to the experimentally determined pose.

In yet another embodiment again, the similarity is based on pairwise comparisons between each ligand in the set of ligands and every other ligand in the set of ligands and pairwise comparisons between the candidate ligand and every ligand in the set of ligands.

In a yet further additional embodiment, the similarity is further based on pairwise comparisons of substructures between each ligand in the set of ligands and every other ligand in the set of ligands and pairwise comparisons between the candidate ligand and every ligand in the set of ligands.

In yet another additional embodiment, the similarity is further based on pairwise comparisons of a biomolecule-ligand interaction between each ligand in the set of ligands and every other ligand in the set of ligands and pairwise comparisons between the candidate ligand and every ligand in the set of ligands.

In a further additional embodiment again, the biomolecule-ligand interaction is selected from a hydrogen bond, a salt bridge, and a hydrophobic interaction.

In another additional embodiment again, determining a pose for the candidate ligand includes determining a pose for each ligand in the set of ligands that minimizes the potential of all ligands.

In a still yet further embodiment again, the potential is determined by:

$$E(L) = (n-1)E^{dock}(L) + E^{pairwise}(L),$$

where L=$(\ell_1, \ldots, \ell_n)$ indexes the candidate poses for each ligand, n is the number of ligands, $E^{dock}$ represents the standard docking scores for the set of ligand poses, and $E^{pairwise}$ represents a pairwise contribution to the total score.

In a yet further additional embodiment again, $E^{pairwise}$ (L)=$\Sigma_{(i,j),i\neq j}e^{pairwise}(\ell_i, \ell_j)$.

In a still yet further additional embodiment, $e^{pairwise}$ is determined using a machine learning algorithm.

In still yet another additional embodiment, the machine learning algorithm is fit to a benchmark set of pairs of correct poses and pairs of incorrect poses for a diverse set of proteins.

In a yet further additional embodiment again, determining a pose for each ligand in the set of ligands includes utilizing an expectation-maximization algorithm.

In yet another additional embodiment again, the method further includes altering a pose of a ligand in the set of ligands or the candidate ligand to optimize that ligand's contribution to the potential function.

In a still yet further additional embodiment again, the biomolecule is selected from a protein, a carbohydrate, a DNA molecule, an RNA molecule, and combinations thereof.

Other features and advantages of the present invention will become apparent from the following detailed description, taken in conjunction with the accompanying drawings which illustrate, by way of example, the principles of the invention.

BRIEF DESCRIPTION OF THE DRAWINGS

The description and claims will be more fully understood with reference to the following figures and data graphs, which are presented as exemplary embodiments of the invention and should not be construed as a complete recitation of the scope of the invention.

FIGS. 1A-11B illustrate ligand docking in accordance with various embodiments of the invention.

FIG. 2 illustrates how ligands adopt similar binding poses accordance with various embodiments of the invention.

FIG. 3 illustrates a flow chart of a method to determine binding pose in accordance with various embodiments of the invention.

FIGS. 5A-5C illustrate exemplary data showing how certain embodiments identify key interactions in accordance with various embodiments of the invention.

FIGS. 6A-6B illustrate exemplary data demonstrating performance of certain embodiments against a diverse benchmarking set in accordance with various embodiments of the invention.

FIG. 7 illustrates a flow chart of a method to determine binding affinity in accordance with various embodiments of the invention.

FIGS. 9A-9D illustrate exemplary data demonstrating prediction and validation of binding poses in accordance with various embodiments of the invention.

DETAILED DESCRIPTION

Turning now to the drawings, systems and methods to predict protein-ligand complexes and uses thereof are provided. Certain embodiments provide methods that substantially improves the accuracy of binding pose prediction by exploiting a widely available source of non-structural information: a list of other ligands that bind the same target. Many embodiments quantify and leverage a chemist's intuition that even very different ligands tend to form similar interactions with a target protein. Further embodiments describe virtual screening methods to identify molecules that bind to targets. Some embodiments further determine a binding affinity for such molecules.

Binding of small-molecule ligands to proteins is one of the most fundamental processes in biology, and the great majority of drugs are ligands that exert their effects by binding to a target protein. Determining a ligand's binding pose—the three-dimensional coordinates of the ligand's atoms when bound to the target—is important for structure-based optimization of the ligand's pharmacological properties, as well as to understanding how it influences its target. Knowledge of a ligand's binding pose is so advantageous that researchers in industry and academia often spend months or years to solve an experimental structure of a particular ligand in complex with a target protein. Knowing binding pose information provides many uses, including rationally designing ligands with desired signaling profiles, increasing potency, sub-type selectivity, and bridging multiple binding sites (e.g., bivalent ligands), among a broad range of other applications. While most commonly used intuitively by chemists, further uses can include structure-based virtual screening, free energy calculations, and/or molecular dynamics simulations.

Additionally, as medicinal chemistry progresses, many current and future therapeutics utilize other macromolecules, including DNA, RNA, peptides, proteins, and carbohydrates as therapeutics or as target molecules of ligands. While much of the description discloses the use on ligand-protein interactions, many embodiments are directed to ligand-macromolecule interactions more generally. Macromolecules can include biomolecules, including (cut not limited to) DNA, RNA, carbohydrate, and proteins. Even more embodiments are directed to using biomolecules as ligands themselves, such that DNA, RNA, peptides, proteins, or carbohydrates interact with proteins or other biomolecules. Additionally, several embodiments utilize ligands comprising small molecules, including organic and/or inorganic molecules. One of skill in the art would understand the following disclosure as enabling for such modifications to allow for such extensions.

Figure 1A:
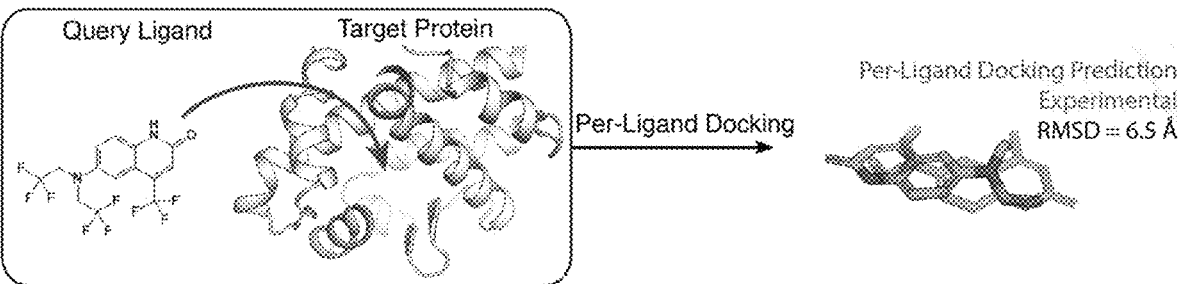

Because experimental structure determination is time-consuming, expensive, and sometimes impossible, tremendous effort has been invested in the development of in silico "docking" methods for predicting ligand binding poses. (See e.g., Allen et al., 2015 DOCK 6: Impact of new features and current docking performance. J Comput Chem 36, 1132-1156; Friesner et al., 2004 Glide: a new approach for rapid, accurate docking and scoring. 1. Method and assessment of docking accuracy. Journal of medicinal chemistry 47, 1739-1749; Friesner et al., 2006 Extra precision glide: docking and scoring incorporating a model of hydrophobic enclosure for protein-ligand complexes. Journal of medicinal chemistry 49, 6177-6196; Jain, 2003 Surflex: fully automatic flexible molecular docking using a molecular similarity-based search engine. Journal of medicinal chemistry 46, 499-511; Jones et al., 1997 Development and validation of a genetic algorithm for flexible docking. Journal of molecular biology 267, 727-748; Kuntz et al., 1982 A geometric approach to macromolecule-ligand interactions. J Mol Biol 161, 269-288; Platzer et al., 1972 CONFORMATIONAL ENERGY CALCULATIONS OF ENZYME-SUBSTRATE INTERACTIONS. II. Computation of the Binding Energy for Substrates in the Active Site of α-Chymotrypsin. International Journal of Peptide and Protein Research 4, 201-219; Rarey et al., 1996 A fast flexible docking method using an incremental construction algorithm. Journal of molecular biology 261, 470-489; Trott and Olson, 2010 AutoDock Vina: improving the speed and accuracy of docking with a new scoring function, efficient optimization, and multi-threading. J Comput Chem 31, 455-461; and Venkatachalam et al., 2003 LigandFit: a novel method for the shape-directed rapid docking of ligands to protein active sites. J Mol Graph Model 21, 289-307; the disclosures of which are hereby incorporated by reference herein in their entireties.) Such methods are considered physics-based or "per-ligand" approaches—i.e., given a structure of the target protein, these docking methods sample many candidate poses of a query ligand and rank these poses using scoring functions that approximate the energetic favorability of each pose. Such scoring functions are typically designed to capture interatomic interactions such as hydrogen bonds and van der Waals forces (FIG. 1A).

Despite the development of dozens of docking software packages over the past 40 years, their performance at pose prediction leaves much room for improvement. Binding pose predictions are typically correct less than half the time for ligands substantially different from those in the experimental structures used for docking.

Figure 1B:
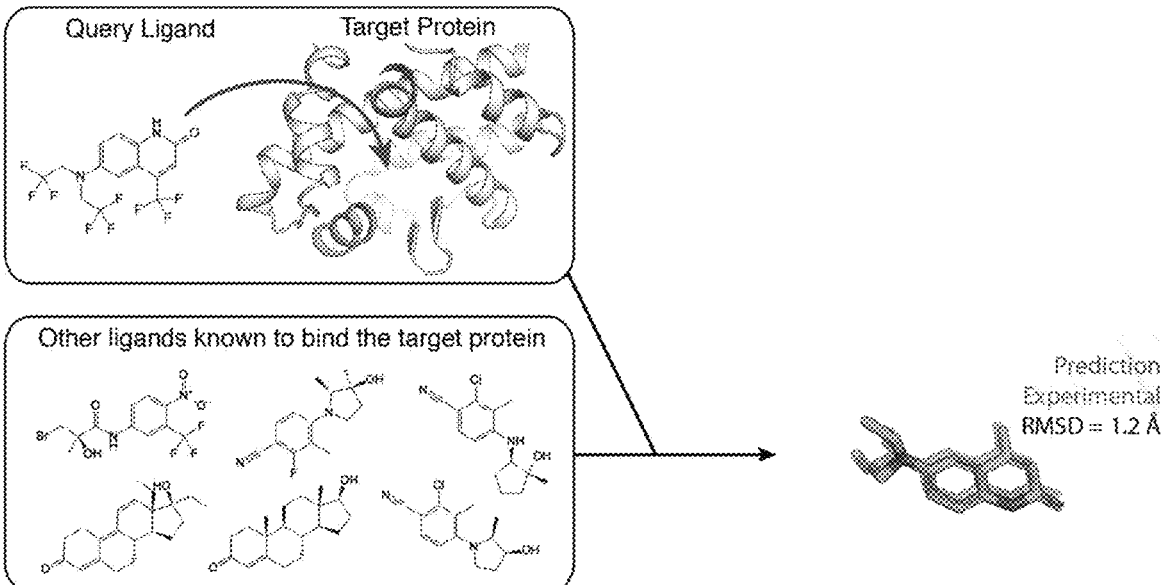

Many embodiments are directed to methods and systems that substantially improve binding pose prediction by using a widely available type of non-structural data, such as the identities of other ligands known to bind the same target (FIG. 1B). Such data is routinely collected in drug development campaigns, both through initial screens to identify lead compounds and through assays of analogs synthesized during lead optimization, and is available in public databases such as ChEMBL for the vast majority of recognized drug targets. (See e.g., Gaulton et al., 2017 The ChEMBL database in 2017. Nucleic Acids Res 45, D945-D954; the disclosure of which is herby incorporated by reference herein in its entirety.)

Figure 2:
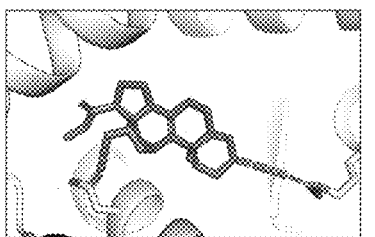
Figure 2:
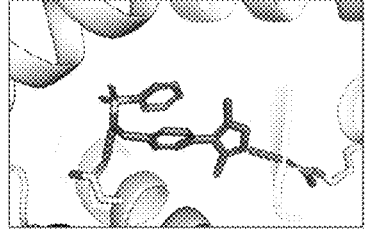
Figure 2:

Medicinal chemists have long recognized that distinct ligands tend to bind a given protein in similar poses; even ligands sharing no common substructure often form similar interactions with the target protein (FIG. 2). This intuition has a sound basis in physics. For example, the energetic favorability of a protein-ligand hydrogen bond depends on the mobility of the protein atoms involved and their ability to form hydrogen bonds with water in the absence of the ligand. (See e.g., Bissantz et al., 2010 A medicinal chemist's guide to molecular interactions. Journal of medicinal chemistry 53, 5061-5084; the disclosure of which is herby incorporated by reference herein in its entirety.) These factors contribute similarly to binding of different ligands but are difficult to predict from a static protein structure alone.

Methods to Identify Ligand-Protein Interaction

Figure 3:
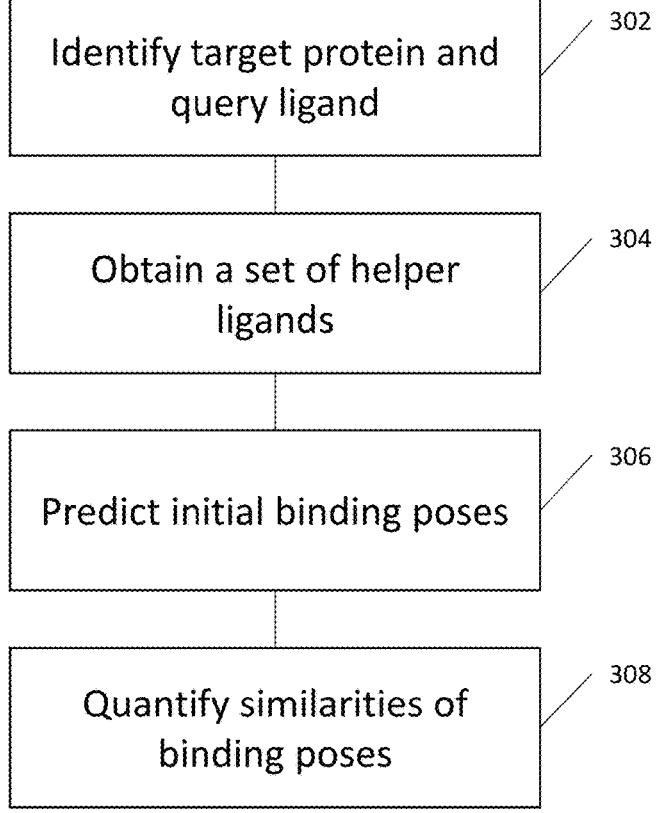

Turning to FIG. 3, various embodiments are directed to methods to identify ligand-protein interaction. The interaction between a ligand and a protein can be identified by its pose, or how a molecule is arranged within the target protein. Specifically, FIG. 3 illustrates an exemplary method 300 to predict binding pose of a ligand. At 302, many embodiments identify a target protein and query ligand. Various embodiments select a target protein and query ligand that are known to interact. In numerous embodiments, the target protein is a drug target. During 302, many embodiments obtain structures for the target protein and query ligand with molecular coordinates, such as through known means or databases, including ChEMBL, PDB, etc.

At 304, additional embodiments obtain a set of structures of ligands known to bind to or interact with the target protein ("helper ligands"). A set, in accordance with various embodiments, can contain any number of ligands, such as at least 1 ligand, at least 2 ligands, at least 5 ligands, at least 10 ligands, at least 20 ligands, at least 50 ligands, at least 100 ligands, or more. In some embodiments, a binding pose for a ligand in the set of ligands is known, such as a binding pose discovered via experimental means.

In some embodiments, the known-binding ligands are obtained from a public database, such as ChEMBL. Various embodiments curate the set of known-binding ligands based on factors such as binding affinity, including high affinity binding and/or sharing a large substructure with the query ligand (congeneric).

At 306, various embodiments predict initial binding poses of the query ligand and set of known-binding ligands to the target protein. Certain embodiments use per-ligand docking software to generate a list of candidate poses for each ligand. Exemplary docking software used in various embodiments includes (but is not limited to) one or more of Glide, DOCK, AutoDock VINA, FlexX, GOLD, and/or Surflex. However, many embodiments can utilize any per-ligand scoring function and pose sampling strategy, including those implemented in any other per-ligand docking package.

Various embodiments utilize the docking software to generate a set of poses for each ligand, including the query ligand and the set of ligands known to bind the target protein. In some embodiments, the set of poses are the highest ranking poses as determined by a scoring function within the docking software. In certain embodiments, the set of ranked poses includes at least 10 poses, at least 25 poses, at least 50 poses, at least 100 poses, or more poses for each ligand.

To dock ligands in some embodiments, a single target protein structure is selected from PDB. Additional embodiments prepare the target protein structure by removing waters, optimizing hydrogen bonds, and performing energy minimization with non-hydrogen atoms constrained to an RMSD of less than 0.3 Å from the initial structure.

Because various embodiments can use any per-ligand docking method for pose generation and scoring of individual ligands, it will be able to take advantage of improvements to these methods. For example, various embodiments use machine learning to fit scoring functions, and others allow for binding pocket flexibility when generating candidate poses.

At 308, many embodiments quantify similarities of binding poses for the query ligand and known-interacting ligand or ligands. Many embodiments solve for all their binding poses simultaneously. Many embodiments quantify similarities based on three-dimensional space, based on coordinates of each atom within the molecules (e.g., ligands and protein). To maximize a scoring function in various embodiments, the per-ligand docking software generates candidate poses and assigns a per-ligand score to each pose. Many embodiments then select a set of poses-one for each ligand—that optimizes the scoring function. In many embodiments, the scoring function considers both the favorability of each ligand's pose, as assessed by a per-ligand scoring function, and the likelihood that a set of poses sharing a given level of similarity is correct or incorrect.

Many embodiments perform pairwise comparisons between every ligand by computing similarities between every pose in a set of poses for one ligand and every pose in a set of poses for a second ligand. Numerous embodiments compute such similarities for every pair of ligands.

When an experimentally determined pose is available for one or more ligands, some embodiments "fix" the pose for a ligand having an experimentally determined pose to the "correct" pose, rather than maintaining a set of candidate poses, where a pose is considered correct if it is within a threshold distance of an experimentally determined pose—for example, within 1 Å, 2 Å, 5 Å, 10 Å, root mean squared deviation (RMSD) to the experimentally determined pose.

Further embodiments evaluate pose similarity for different types of protein-ligand interactions, including hydrogen bonds, salt bridges, and hydrophobic contacts. Quantitative measures used in various embodiments are designed to assess the presence of these interactions between the ligand and a given protein residue. In many embodiments, the hydrogen bond and salt bridge interaction measures are designed to give a value of 1 for interactions meeting established criteria. A soft boundary is added to give borderline cases values between 0 and 1, in order to prevent discontinuities in some embodiments. The hydrophobic contact measure approximates the hydrophobic surface contact area by considering the number of protein-ligand atom pairs in contact with each other. Again, a soft boundary (in this case, between an atom pair being or not being in contact) can be used to prevent very similar poses from leading to very different values. Various embodiments denote the interaction value for interaction type k, for pose $\ell_i$ of ligand i, with protein residue r as $$X_r^{(k)}(\ell_i).$$

Interaction similarities for a pair of poses (for two different ligands bound to the same target protein) are computed separately for each interaction type in various embodiments. The interactions made between the ligand and each residue of the target protein residue can be tabulated and then the similarity between the resulting lists for each pose can be measured by the Tanimoto coefficient. The Tanimoto coefficient can be modified by the addition of pseudo counts, which serve to make the metric well defined if neither ligand forms a particular type of interaction and to reward poses that share larger numbers of interactions in absolute terms. Certain embodiments define the interaction similarity, for interaction type k between a pair of poses $\ell_i$, $\ell_j$ (for ligands i and j, respectively), as $$s^{(k)}(\ell_i, \ell_j) = \frac{1 + \sum_{r \in R} \sqrt{X_r^{(k)}(\ell_i) X_r^{(k)}(\ell_j)}}{2 + \sum_{r \in R}[X_r^{(k)}(\ell_i) + X_r^{(k)}(\ell_j)] - \sum_{r \in R} \sqrt{X_r^{(k)}(\ell_i) X_r^{(k)}(\ell_j)}},$$

where R is the set of all protein residues.

In various embodiments, when computing hydrogen bond similarity, a case where a given protein residue acts as a hydrogen bond donor for one ligand and a hydrogen bond acceptor for another ligand is not considered a shared interaction.

Figure 4A:
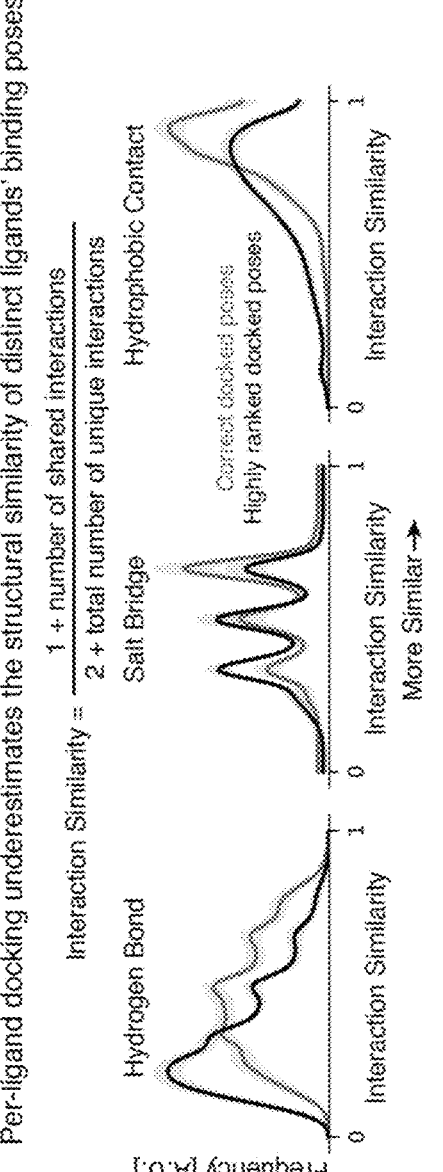
FIG. 4A-4B illustrate exemplary data of interaction and substructure similarity in accordance with various embodiments of the invention.

FIG. 4A illustrates exemplary data illustrating interaction similarity in correct and highly ranked poses, where pairs of correct poses form more similar interactions than other pairs of poses ranked highly by the per-ligand scoring function.

Figure 4B:
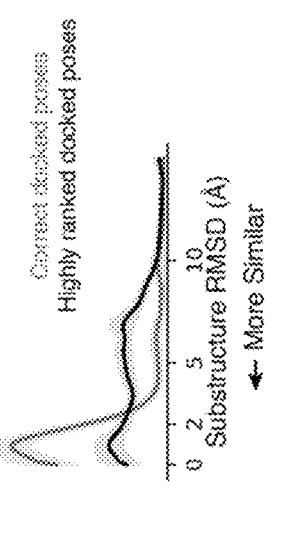

Additional embodiments define a substructure similarity as the RMSD of atom positions of the largest chemical substructure shared by a pair of ligands. Certain embodiments evaluate substructure similarity for pairs of ligands that shared a substructure at least half the size of the smaller ligand. FIG. 4B illustrates exemplary data showing that for this similarity metric, too, the native distribution exhibits higher similarity than the reference distribution, indicating that the common substructure tends to be more similarly positioned in pairs of correct poses than in other pairs of poses ranked highly by the per-ligand scoring function.

Many embodiments compute the substructure similarity for a pair of candidate poses. To compute the substructure similarity, the maximum common substructure of the two ligands can be identified using available software (e.g., Canvas from Schrodinger LLC) and then mapped onto each candidate pose. Finally, the RMSD between these two sets of atoms can be computed and used as the measure of substructure similarity. Certain embodiments define custom atom and bond types for computation of the common scaffold. Scaffold similarity is not considered for pairs of ligands with a maximum common substructure of less than half the size of the smaller ligand in certain embodiments. Various embodiments do not include hydrogen atoms in the substructure nor when determining the total number of atoms in each ligand.

The scoring function of various embodiments is derived by quantifying the medicinal chemist's intuition that different ligands tend to adopt structurally similar poses when binding the same target protein. By quantifying such assumptions, these embodiments seek not only to measure the similarity of correct poses of different ligands, but also to compare the similarity of correct poses to that of other poses ranked highly by per-ligand docking software. Additionally, two notions of similarity are considered: similarity of protein-ligand interactions and similarity in position of common ligand substructures.

Using a benchmark set of protein-ligand complex structures, many embodiments characterize the extent to which distinct ligands binding a common target adopt similar poses, as quantified by the interaction and substructure similarity metrics described above.

Some embodiments use a curated set of protein-ligand complex structures representing major drug targets. (See e.g., Santos et al., 2017 A comprehensive map of molecular drug targets. Nature reviews Drug discovery 16, 19-34; the disclosure of which is hereby incorporated by reference herein in its entirety.) Some of these embodiments use one or more of manual curation and adaption of a PDBbind refined set. (See e.g., Wang et al., 2005 The PDBbind database: methodologies and updates. Journal of medicinal chemistry 48, 4111-4119; the disclosure of which is hereby incorporated by reference herein in its entirety.)

Some embodiments generate a probability distribution based on the "correct pose" similarities, and various embodiments store the probability distribution as a native distribution. Additional embodiments determine quality of docked poses. In certain embodiments, the accuracy of each pose is quantified by the non-hydrogen-atom RMSD from the experimentally determined pose. Various embodiments compute the RMSD by aligning each complex to the structure used for docking based on non-hydrogen-atoms within 15 Å of the ligand, and an RMSD is then computed between the docked pose and the same ligand's pose in the aligned complex. Some embodiments consider poses with within 2.0 Å RMSD to be "near-native" or "correct".

When computing these statistics, various embodiments identify docked poses that are near-native among the candidate poses ranked in the top 100 by the docking software.

Certain embodiments use these docked poses, as opposed to the experimentally determined pose, in order to ensure that the statistics will be applicable to the scoring of candidate poses generated by docking software. Additional embodiments compute the empirical distribution of each similarity type (e.g., substructure, interaction, etc.) across all pairs of near-native poses using a Gaussian kernel density estimate with standard deviation of 0.03 for interaction similarities and 0.18 for substructure similarities. To reduce bias near the boundaries, reflected boundary conditions are applied in some embodiments. Some embodiments cap substructure similarities at 6 Å (that is, substructure similarities greater than 6 Å were set to 6 Å), as the sparsity of near-native pose pairs for higher values led to overly rough distributions. However, additional embodiments can cap substructure similarities to another threshold, as optimized for a particular use. Various embodiments denote the similarity distribution over near-native poses for interaction type k as $f_k(x;$ Native).

Many embodiments compute equivalent similarity distributions using all pairs of candidate poses produced by the docking software, regardless of whether they are near-native. Certain embodiments denote the resulting distributions as $f_k(x;$ Reference).

To combine the distributions for the four similarity types into a single joint distribution, many embodiments assume that the interaction types are conditionally independent and express the joint distribution as a product of the distributions for each interaction type. That is:

$$f(s(\ell_i, \ell_j); \text{Native}) = \prod_k f_k\left(s^{(k)}(\ell_i, \ell_j); \text{Native}\right)$$

$$f(s(\ell_i, \ell_j); \text{Reference}) = \prod_k f_k\left(s^{(k)}(\ell_i, \ell_j); \text{Reference}\right)$$

where $s(\ell_i, \ell_j)$ is the vector of $s^{(k)}(\ell_i, \ell_j)$'s for each similarity type k.

Further embodiments can use any additional pairwise pose similarity metric. Various embodiments could potentially improve performance by using more fine-grained interaction descriptors or by using similarity metrics based on field-based methods developed for virtual screening.

Certain embodiments derive a statistical potential for sets of binding poses. Many embodiments use the similarity distributions (e.g., reference and native) to derive a statistical potential that-instead of acting on features of a single pose, as in previous docking software-acts on a set of hypothesized poses, one for each ligand, known to bind the target protein. In a number of embodiments, potential is determined by the equation:

$$E(L) = (n-1)E^{dock}(L) + E^{pairwise}(L),$$

where $L=(\ell_1, \ldots, \ell_n)$ indexes the candidate poses for each ligand, n is the number of ligands, $E^{dock}$ represents the standard docking scores for the set of ligand poses, and $E^{pairwise}$ represents the pairwise contribution to the total score. In some embodiments, $$E^{pairwise}(L) = \sum_{(i,j),i \neq j} e^{pairwise}(\ell_i, \ell_j).$$

Various embodiments determine $e^{pairwise}$ is determined utilizing one or more machine learning models. Some machine learning models fit to a benchmark set of pairs of correct poses and pairs of incorrect poses for a diverse set of proteins.

Additional embodiments utilize the following equation to determine potential:

$$E^{ComBind}(\text{Poses for a set of ligands}) =$$

$$(n-1)\sum_{ligands} E^{dock}(\text{pose}) + \sum_{ligand\,similarity}\sum -\log$$

$$\frac{\text{frequency of pair similarity in native distribution}}{\text{frequency of pose pair similarity in reference ditribution}},$$

where n is the total number of ligands.

In the above equation, the first component evaluates the energetic favorability of each ligand's pose individually using a per-ligand scoring function $E^{dock}$ (e.g., a scoring function used in Glide or another docking software package). The summation is over ligands known to bind the target protein, with "pose" referring to the hypothesized pose for each ligand.

The second component rewards sets of poses with a degree of similarity that is more often observed in correct poses than in other poses ranked highly by the per-ligand scoring function. Here, the outer summation is over pairs of distinct ligands known to bind the target protein, and the inner summation is over the interaction and substructure similarity measures (see FIGS. 4A-4B): hydrogen bond similarity, salt bridge similarity, hydrophobic contact similarity, and substructure similarity. "Pose pair similarity" refers to the calculated similarity value of the given type for the hypothesized poses of the given ligand pair. The "native distribution" and "reference distribution" for each similarity type are determined as described above. The resulting negative log likelihood ratios have the mathematical properties of an energy, namely that an additive decrease in energy corresponds to a multiplicative increase in likelihood ratio, allowing for straightforward integration with standard per-ligand docking scores, which are typically in units of energy. For pairs of ligands that do not share a substructure at least half the size of the smaller ligand, the substructure similarity term can be excluded in the summation.

The second component acts as a correction to the first. If the per-ligand scoring function were perfect, in the sense that it could perfectly distinguish correct poses from incorrect ones, the terms in the second component would consistently assume values of zero. Because per-ligand scoring functions remain imperfect—and, in particular, tend to underpredict the likelihood that a set of ligands will adopt similar poses—the second component typically assumes non-zero values.

The statistical potential used by various embodiments is sufficiently general that the method could be extended to exploit other types of data, ranging from multiple experimental structures of the protein in complex with different ligands to effects of protein mutation on ligand binding. Likewise, various embodiments exploit the affinity of each known binder.

It should be noted that various embodiments may perform various steps simultaneously, multiple times, and/or omit steps as appropriate for a particular use. For example. Some embodiments may obtain multiple query ligands and/or multiple sets of known-binding ligands for use within an embodiment of method 300. Additionally, certain embodiments iteratively change a pose for a ligand to optimize that ligand's contribution to the potential function, such that multiple features of method 300 may be repeated.

Figure 5:
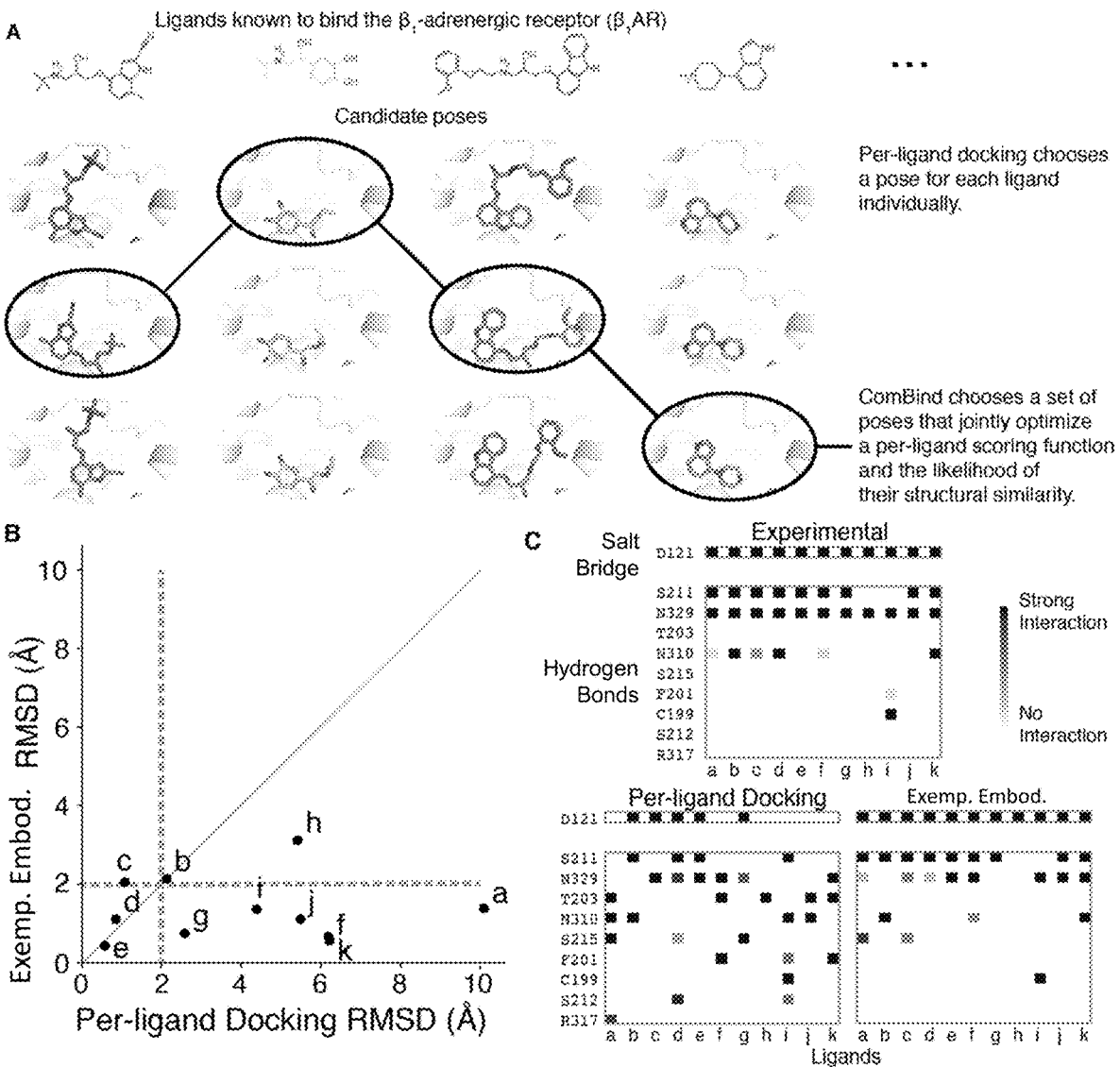

Turning to FIGS. 5A-5C, exemplary data showing the improvement of many embodiments is illustrated. Specifically, FIG. 5A illustrates a comparison between various ligands known to bind to the $\beta_1$-adrenergic receptor ($\beta1AR$). Typical docking software (e.g., Glide) evaluate each ligand independently. In contrast, many embodiments evaluate multiple poses for multiple ligands simultaneously to provide poses (circled) that minimize potential. When the poses identified by the docking software and exemplary embodiment were compared to experimentally determined poses, FIG. 5B illustrates that Glide (X-axis) correctly identified only 4 out of 11 poses (left of 2 Å dashed line), while the exemplary embodiment (Y-axis) correctly identified 10 of the 11 poses (below 2 Å dashed line). Additionally, FIG. 5C illustrates a comparison of experimentally determined protein-ligand interactions between Glide (Per-ligand Docking) and the exemplary embodiment, showing that the exemplary embodiment is more similar to the experimentally determined interactions.

Figure 6:
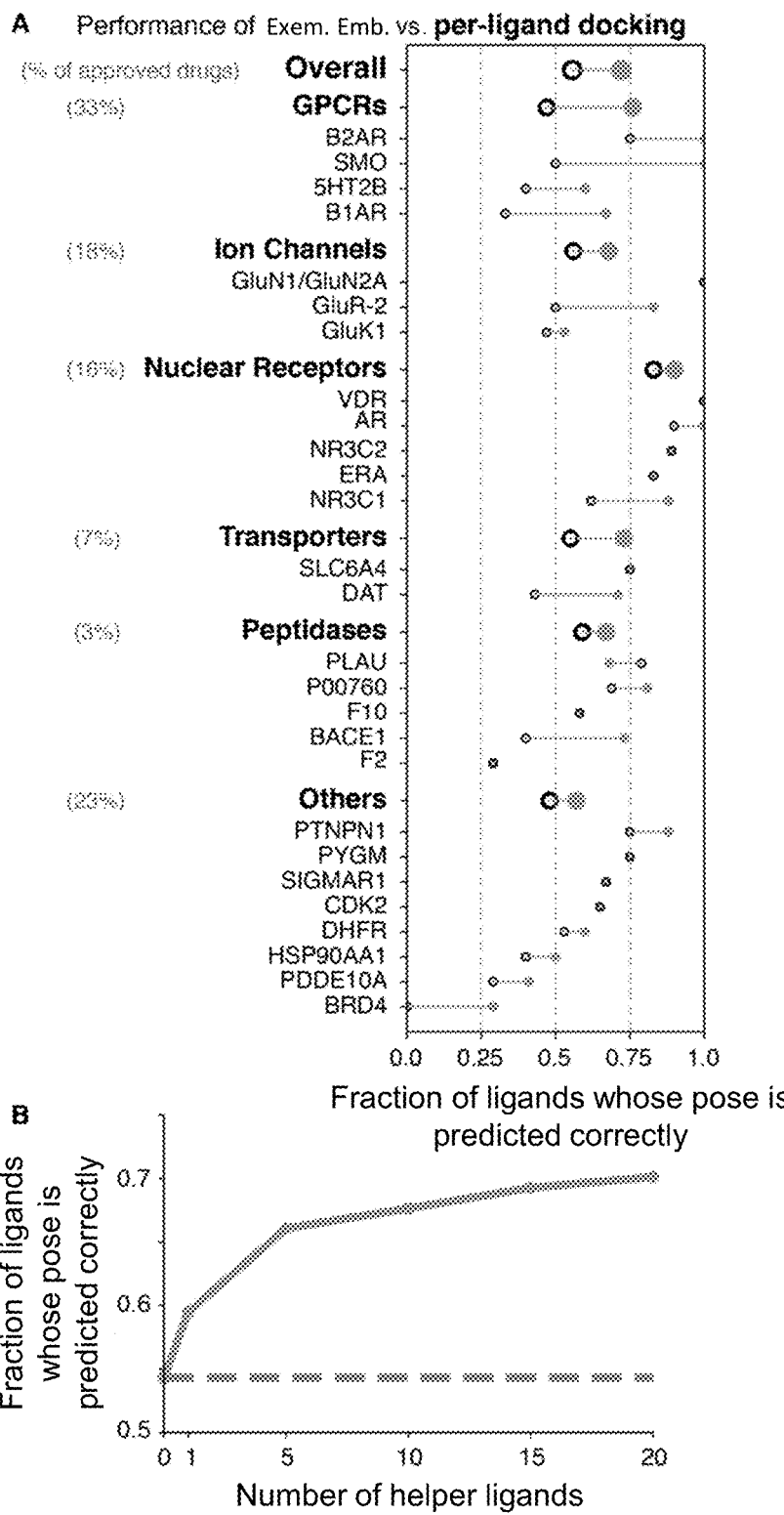

Similarly, FIGS. 6A-6B illustrate exemplary data of the improvements provided by embodiments over per-ligand docking software (e.g., Glide). Specifically, when benchmarked against a set of 245 protein-ligand complexes representing major families of drug targets. FIG. 6A illustrates an improvement provided by the embodiment (dots) over Glide (open circles) for the various protein families. On average, these exemplary embodiments select a correct binding pose 30% more frequently. For G-protein-coupled receptors (GPCRs), which are of particular interest both because they represent the largest family of drug targets and because their structures are notoriously difficult to determine experimentally, various embodiments select a correct binding pose over 60% more frequently, increasing the probability of correct prediction from 47% to 76%. FIG. 6B illustrates an improvement provided by the known-binding, or helper, ligands. As illustrated in FIG. 6B, increasing the size of the set of known-binding (helper) ligands improves performance of some embodiments.

Virtual Screening

Further embodiments are directed to methods to identify ligands that bind to a target protein from a query set, utilizing prior knowledge of one or more molecules that bind the target protein. Some of these embodiments identify which molecules from a query set that bind to the target protein, then identify a binding affinity for any molecule that binds to the target protein. Some embodiments further provide rankings or other information for any molecules that are determined to bind to a target protein. Such embodiments can assist in many uses, such as pharmaceutical lead optimization and virtual screening of molecules.

Some embodiments are used in drug discovery to identify drug candidates that may interact with target proteins. However additional embodiments are used in cellular signaling (e.g., binding of hormones and neurotransmitters), sensation (e.g., binding of odorants and flavorants), enzyme function (e.g., binding of nutrients and other metabolic substrates), and defense mechanisms (e.g., binding of toxins and antibiotics). Pose prediction is used to understand the effects of genetic variation on responses to both naturally occurring ligands and drugs, which can benefit personalized medicine. In each of these cases, multiple ligands are typically known to bind the targets of interest, and certain embodiments may thus be used to improve binding pose prediction.

Figure 7:
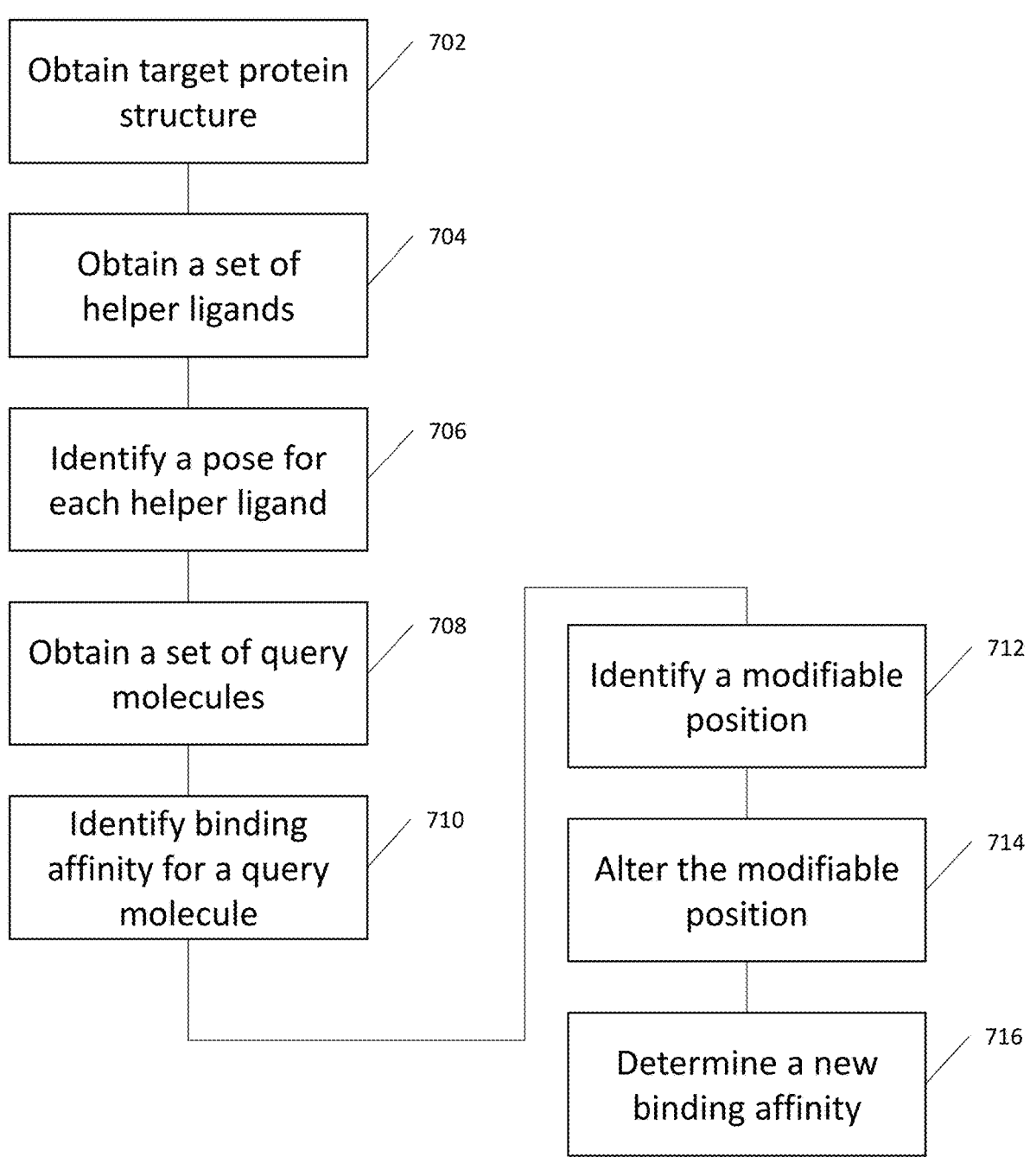

FIG. 7 illustrates an exemplary method 700 for determining a binding affinity for a molecule in accordance with various embodiments. Many embodiments obtain a structure of a target protein at 702. In numerous embodiments, the target protein is a drug target. Some embodiments obtain a structure for the target protein with molecular coordinates, such as through known means or databases, including ChEMBL, PDB, etc.

Many embodiments obtain a set of structures of ligands known to bind to or interact with the target protein ("helper ligands") at 70. A set, in accordance with various embodiments, can contain any number of ligands, such as at least 1 ligand, at least 2 ligands, at least 5 ligands, at least 10 ligands, at least 20 ligands, at least 50 ligands, at least 100 ligands, or more. In some embodiments, a binding pose for a ligand in the set of ligands is known, such as a binding pose discovered via experimental means.

In some embodiments, the known-binding ligands are obtained from a public database, such as ChEMBL. Various embodiments curate the set of known-binding ligands based on factors such as binding affinity, including high affinity binding and/or sharing a large substructure with the query ligand (congeneric).

At 706, various embodiments identify a pose for each ligand in the set of helper ligands. Such methods are similar to the docking and pose prediction as described in method 300 (see FIG. 3 and associated text), although, method 700 may not include simultaneous docking of a query ligand or molecule. Many embodiments "fix" or hold a single pose for each helper ligand as a permanent binding pose.

At 708, many embodiments obtain a set of query molecules. The set of query molecules can include any number of molecules, including 1 molecule, 2 molecules. 3 molecules, 4 molecules, 5 molecules, 10 molecules 15 molecules, 20 molecules, 25 molecules, 50 molecules, 75 molecules, 100 molecules, or more. Many embodiments obtain structures for the query molecules including coordinates for each atom in the molecule.

At 710, many embodiments identify if each query molecule binds to the target protein and generates a binding affinity for each binding molecule. Numerous embodiments utilize a similar procedure as described in method 300 to determine pose. Further embodiments select a pose that minimizes the potential with respect to the helper ligands. In doing so, the minimized potential demonstrates an increased binding affinity between the query molecule and the target protein.

Further embodiments perform lead optimization of one or more query molecules at 712-716. In various embodiments, a modifiable location is identified on the query ligand at 712. The modifiable position can be any position that may allow for additional modification that allows for a change in chemical group, including groups that may sit internal to a binding site that could increase binding affinity, while some embodiments may identify a location that may not contribute to binding, such that a modification could be used for increasing solubility, labeling, or conjugating additional molecules to the query molecule.

At 714, some embodiments alter the modifiable position. For example, some embodiments may alter the position to increase binding affinity via the inclusion of a chemical group that may form an interaction with the target protein, such as via a hydrogen bond, salt bridge, and/or hydrophobic interaction.

Additional embodiments determine a new binding affinity for the modified query molecule at 716. Such binding affinity is assessed similarly to 710, where the pose prediction and potential demonstrate a binding affinity for the modified query molecule.

It should be noted that various embodiments may perform various steps simultaneously, multiple times, and/or omit steps as appropriate for a particular use. For example. Some embodiments may obtain multiple query ligands and/or multiple sets of known-binding ligands for use within an embodiment of method 700.

Figures 8A, 8B:
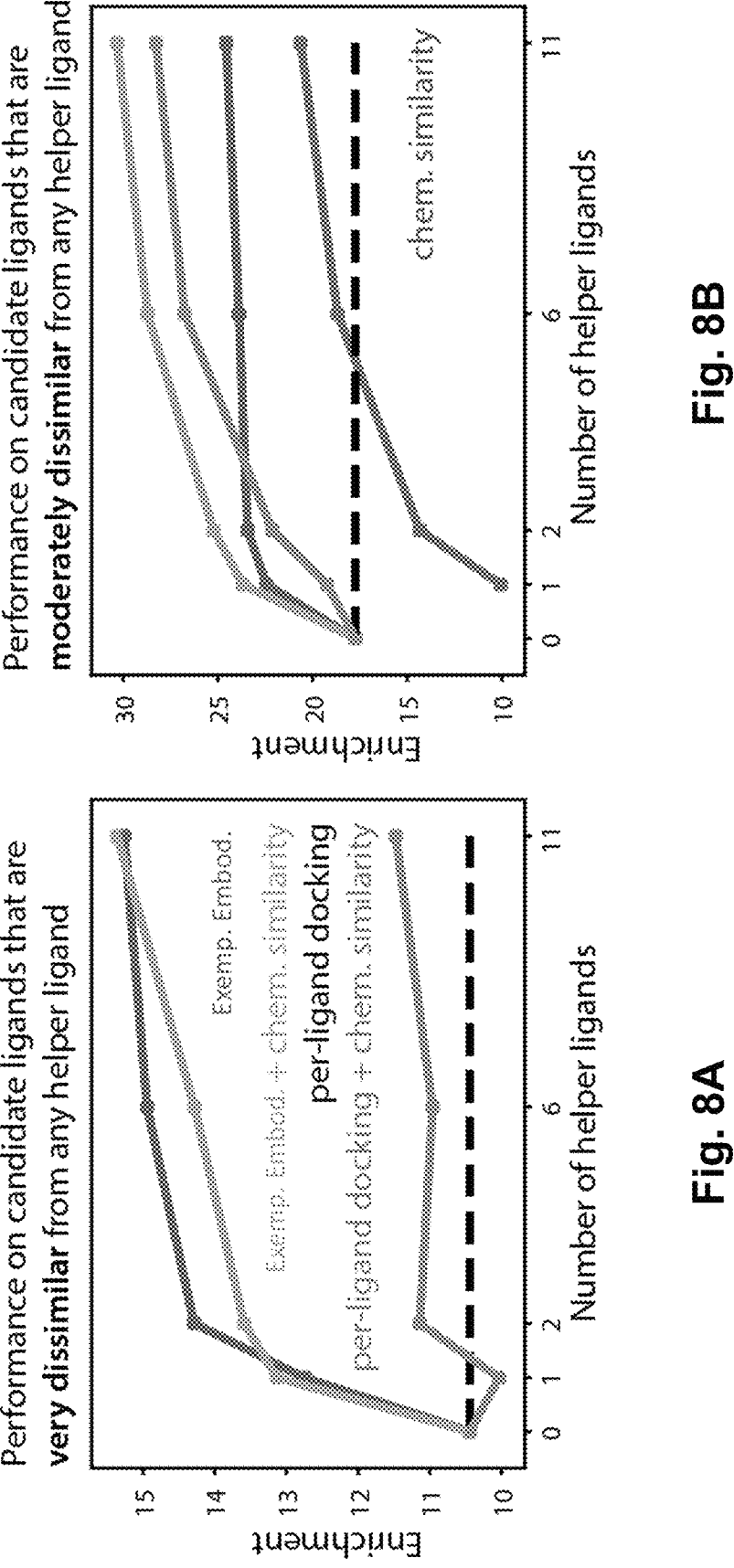
FIGS. 8A-8B illustrate exemplary data of virtual screening performance in accordance with various embodiments of the invention.

Various embodiments perform better at identifying ligands from query sets than current methods. FIGS. 8A-8B illustrate exemplary performance metrics of various embodiments against a per-ligand docking software. Specifically, FIG. 8A illustrates a performance increase with increasing numbers of helper ligands. Helper ligands include In FIG. 8A, the query molecules possessed a Tanimoto Coefficient of <0.20 relative to the helper ligands, while in FIG. 8B, the query molecules possessed a Tanimoto Coefficient of >0.20 and <0.30 relative to the helper ligands. In FIGS. 8A-8B, "chem. similarity" is based on the presence of similar chemical groups between the query molecule and helper ligands.

EXEMPLARY EMBODIMENTS

Although the following embodiments provide details on certain embodiments of the inventions, it should be understood that these are only exemplary in nature, and are not intended to limit the scope of the invention.

Example 1: Structure Prediction Informed by Non-Structural Data

As an illustrative example, one embodiment was used to predict binding poses for ligands at the $\beta_1$-adrenergic receptor ($\beta$1AR), the primary target of the beta blocker drugs that are widely used to treat heart attack, heart failure, and hypertension. Eleven diverse ligands known to bind $\beta$1AR were selected, including both beta blockers and beta agonists. The 11 distinct ligands were docked to a crystallographic $\beta$1AR structure using Glide, producing up to 100 candidate poses for each ligand. This embodiment solved for a set of poses-one per ligand—that minimizes the potential (FIG. 5A). The crystallographic $\beta$1AR structure used for docking was determined in complex with a ligand distinct from any of the 11 docked ligands. Crystallographic ligand poses were not used in any way by Glide or this embodiment.

Glide's top-ranked pose was correct for 4 of 11 ligands, whereas the pose selected by this embodiment was correct for 10 of 11 ligands (FIG. 5B). In the selected poses for this embodiment—as in experimentally determined poses-most of the ligands form a salt bridge with D121 and hydrogen bonds with S211 and N329 (FIG. 5C). In comparison, the poses ranked most highly by Glide's per-ligand scoring function exhibited more varied hydrogen bonds and salt bridges (FIG. 5C).

It is emphasized that this embodiment did not require that all ligands adopt similar poses or form similar interactions. This embodiment correctly predicted, for example, that two of these $\beta$1AR ligands do not form a hydrogen bond with S211.

In another exemplary embodiment, 245 protein-ligand complexes representing all major families of drug targets were used to benchmark this embodiment. Additionally, several steps to mimic a real-world use case for this embodiment. First, when predicting the binding pose of a query ligand with this embodiment, helper ligands selected from the public ChEMBL database were used. No experimental information on poses of helper ligands were used; indeed, for the vast majority of helper ligands selected, poses have not been determined experimentally. Second, target protein structure determined in the presence of a ligand that shares a chemical scaffold with the query ligand were not used either. Finally, when predicting ligand binding poses at a given target protein, all structures involving that protein when constructing the distributions used to define the potential were omitted.

When comparing this embodiment to Glide, two helper ligand selection criteria were used: (1) a diverse set of ligands with the highest binding affinity ("high affinity"), and (2) the ligands sharing the largest substructure with the query ligand ("congeneric"). Both of these selection criteria lead to substantial performance improvements over Glide, indicating that this embodiment could be applied effectively using either a diverse set of ligands identified from a high-throughput screen or a congeneric series of ligands generated during lead optimization.

Additionally, performance improves with the use of more helper ligands (FIG. 6B). Interestingly, this embodiment substantially outperforms Glide even when using only a single helper ligand.

Example 2: Benchmarking Against State-of-the-Art Software

Methods: The performance of this embodiments was evaluated on 30 target proteins. Only ligands that have less than 50% scaffold overlap with the ligand that was originally present in the experimental structure used for docking were considered. It was found that ligands with higher scaffold overlap were substantially easier to dock, likely due to the binding pocket being well shaped to accommodate the similar ligand. Additionally, only consider for which there is at least one correct candidate pose were considered, since only in these cases is it possible for either this embodiment or Glide to make a correct prediction.

For each of the 245 unique ligands meeting these criteria, other ligands known to bind the respective target protein from the ChEMBL database were identified and then used this embodiment to jointly predict their binding poses. Importantly, when evaluating the performance of this method on a particular target protein, the data for that target protein from the similarity statistics were excluded.

Selecting Helper Ligands: For all targets, Ki or $IC_{50}$ data (whichever was more numerous) from ChEMBL were downloaded. Ligands were removed that did not meet the following criteria: a ChEMBL confidence score of 9 (the highest value), molecular weight <800 Da, and Ki or $IC_{50}$<1 µM. Ligand structures were generated from the SMILES strings provided by ChEMBL.

Two criteria were benchmarked for selecting which ChEMBL ligands to use as helper ligands for each query ligand: (1) the highest affinity binders that do not share a chemical scaffold, and (2) the ligands that share the largest chemical substructure with the query ligand. To define the size of the common substructure, the same maximum common substructure definition as that used to compute substructure similarity were used. For selection method (1), helper ligands were added in order of affinity, not adding a ligand if it has greater than 80% substructure overlap with any ligand already in the selected set of helpers.

The benchmarking results presented in the figures were obtained using the following ligand selection criteria and number of helper ligands: FIG. 6A: 20 helper ligands selected using criterion (1); FIG. 6B: the indicated number of ligands selected using criterion (1). For a handful of targets, fewer than 20 helper ligands were available meeting our criteria. In these cases, we used the minimum of the indicated number of ligands and the number of available ligands. Targets with only one ligand are omitted from FIG. 6A.

Performance Evaluation: An overall performance metric was developed to represent the expected performance in drug development campaigns. For each protein family, the average performance was computed, then weighted each by the fraction of FDA-approved drugs targeting the protein family.

Results: Turning to FIG. 6A, benchmark results of an embodiment are illustrated. In particular, 20 helper ligands for each query ligand were used and selected from ChEMBL by the high-affinity criterion. When evaluating the ability of both per-ligand docking (e.g., Glide) and the one embodiment to select a correct pose from a list of candidate poses, query ligands with at least one correct pose in the list were considered. When computing overall results, target families were averaged across, the performance for each family by the fraction of FDA-approved drugs targeting that family were weighted.

On average, this embodiment selects a correct pose for 72% of ligands, a 30% improvement over Glide. This embodiment proves particularly effective on certain target families. But this embodiment improves pose prediction performance for all target families considered. Even at the individual target level, this embodiment hardly ever degrades performance: this embodiment only reduced performance for one of the 30 targets considered, and this performance reduction was minor.

Removing any of the similarity types from the potential reduced this embodiment's performance. In particular, both protein-ligand interaction similarity and substructure similarity contribute substantially to this embodiment's accuracy. Protein-ligand interaction similarity is the more important of the two, particularly when using a diverse set of helper ligands.

Example 3: Predicting Binding Poses of Antipsychotics at the $D_2$ Dopamine Receptor To illustrate the practical application of embodiments, it was predicted that the previously unknown binding poses of several antipsychotic drugs that target the $D_2$ dopamine receptor ($D_2R$): pimozide, benperidol and spiperone. Only the available structure of $D_2R$ was used, which was determined in complex with risperidone, a ligand substantially different from any of those considered.

Figure 9:
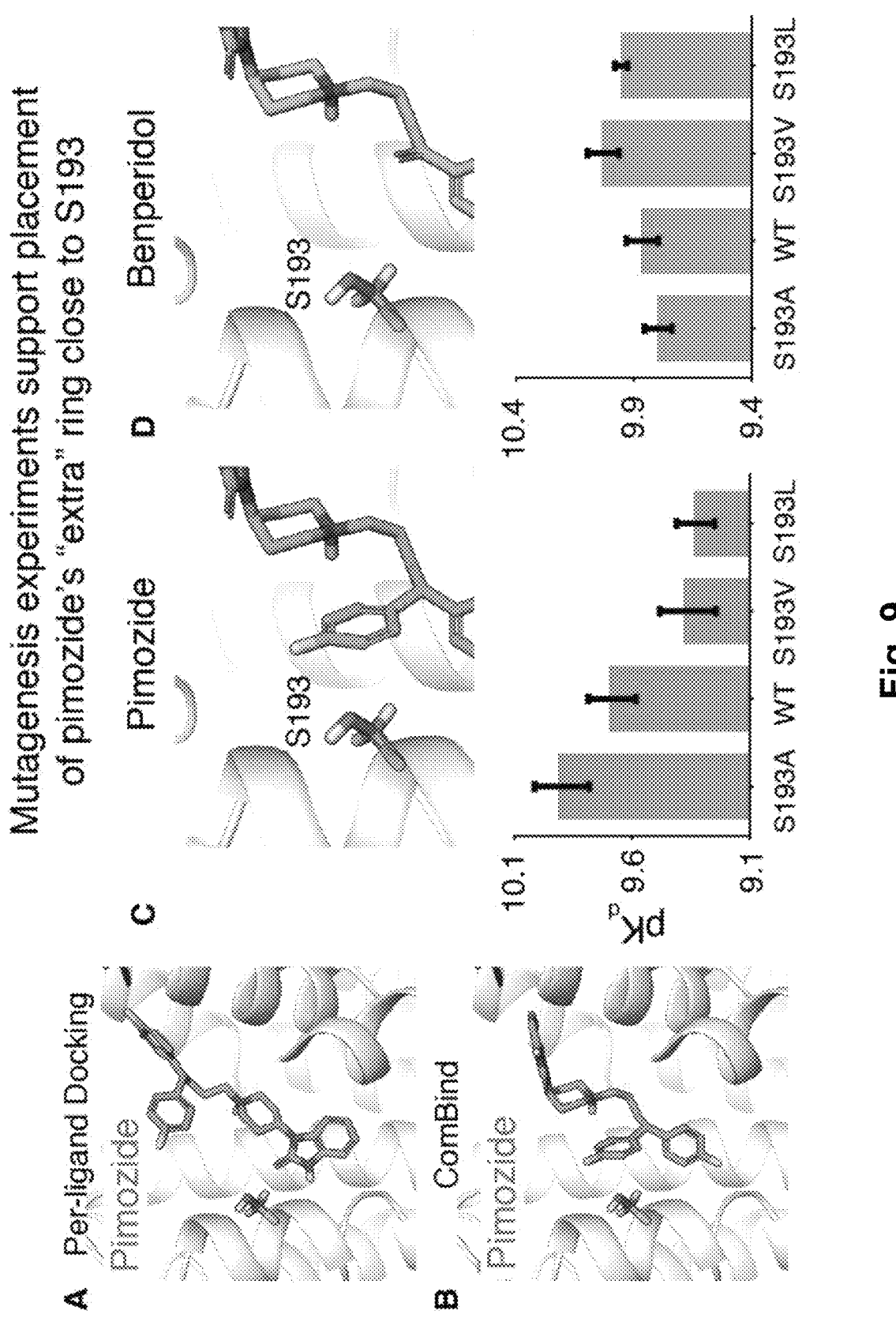

It was predicted that binding poses for pimozide, benperidol and spiperone, as well as the tool compound mespiperone, using both Glide and an embodiment. For spiperone and mespiperone, An embodiment and Glide predicted similar poses. For pimozide and benperidol, however, an embodiment's predictions were very different from Glide's: a fluorobenzene ring of each compound was positioned near the top of the binding pocket by Glide and near the bottom by this exemplary embodiment (FIGS. 9A-9B).

To test the embodiment's predictions, mutagenesis experiments were designed. First, a series of mutations of Ser193 (S193) were tested, which is positioned close to the second fluorobenzene ring of pimozide in the embodiment's predicted pose but not in Glide's (FIG. 9C). Indeed, mutating S193 to a larger residue (Val or Leu) decreases pimozide's affinity, while mutating S193 to a smaller residue (Ala) increases pimozide's affinity. Such effects are not observed for benperidol, which is identical to pimozide except that it lacks the fluorobenzene ring that contacts S193 in pimozide (FIG. 9D). Indeed, benperidol's affinity actually increases when S193 is mutated to a larger residue. These results are consistent with predicted poses of embodiments but not with Glide's: Glide predicts that pimozide and benperidol position nearly identical chemical groups in essentially identical positions near S193.

Mutations to several residues surrounding the top and bottom of the binding pocket were also considered. Unlike Glide, the embodiment predicts that all four ligands will position a fluorobenzene ring at the bottom of the binding pocket, packing favorably against Trp386 (W386). Indeed, mutating W386 to a smaller residue (Phe) reduced affinity to a similar extent for all of the ligands, with a slightly smaller effect for pimozide, which packs less tightly against W386 according to the embodiment's prediction. At the top of the ligand binding pocket, near Val91 and Trp100, the embodiment predicts that the pimozide and benperidol will place identical functional groups that differ somewhat from those of spiperone and mespiperone. Indeed, mutation of these residues affects pimozide and benperidol slightly differently from spiperone and mespiperone.

Binding poses were predicted for the typical antipsychotics spiperone, mespiperone, benperidol, and pimozide at the $D_2$ dopamine receptor (D$_2$R). The ligands were prepared using the Schrodinger ligprep tool, considering the unprotonated tautomer and both inversions of the protonated tautomer. The same docking protocol was used as described above, except that the top 300 poses were considered by this embodiment, in order to account for the use of the 3 tautomeric states of the ligand.

Example 4: Binding Score

This embodiment includes hypothesized set of binding poses of a set of n ligands as L=$\ell_1$, $\ell_2$, ..., $\ell_n$, where $\ell_i$ specifies the hypothesized pose for ligand i.

Per-ligand scoring functions, which consider each ligand independently, would determine an optimal set of poses $\hat{L}$ by choosing the binding pose with minimum docking score for each ligand or, equivalently, by minimizing $$E^{dock}(L) = \sum_{i=1}^{n} E^{dock}(\ell_i)$$

where $E^{dock}(\ell_i)$ is the output of a per-ligand scoring function (such as that reported by Glide) for pose $\ell_i$ of ligand i.

Pairwise terms that tend to favor sets of similar poses were added $$E^{ComBind}(L) = (n-1)E^{dock}(L) + \sum_{(i,j),i \neq j} -\log \frac{f(s(\ell_i, \ell_j); \text{Native})}{f(s(\ell_i, \ell_j); \text{Reference})}.$$

Intuitively, these pairwise terms reward pose pairs with similarity values more often observed in near-native (correct) pose pairs than in reference pose pairs (i.e., pose pairs chosen at random from among all candidates). The idea of comparing the distribution of features in correct solutions to the distribution in all possible solutions has been used in statistical potentials for biomolecular structure prediction and in the naïve Bayes machine learning model. The docking scores were weighted by the number of ligands minus 1, in order to hold the relative contribution of singleton and pairwise terms constant for different numbers of helper ligands.

Consistent with their reported units of kcal/mol, it was found that Glide scores have the mathematical properties of an energy; namely, the negative log likelihood ratio of a pose being near-native is linear in its Glide score. By construction, the pairwise terms we introduce in this study also have this property. This congruence implies that these singleton and pairwise terms can be additively combined (as this is the equivalent of multiplying likelihood ratios).

In general, it could be that the per-ligand docking scores need to be scaled by a constant factor in order to be consistent with the pairwise terms. For example, if the docking scores were on average 10 times the negative log likelihood ratio of a pose being near-native, they would need to be scaled by $1/10$. This constant factor can be identified by performing logistic regression with the docking scores as features and whether each pose is near-native as the response. For Glide scores, the appropriate constant is close to 1 (1/0.9=1.1), and we chose to set it to 1 for simplicity.

Example 5: Optimization

This embodiment used coordinate descent to compute a set of poses that minimizes the binding score. At first, L is randomly initialized. L is then iteratively improved by iterating through the ligands, in a random order, and updating the selected ligand's pose to the argument minimum of $E^{ComBind}(L)$ assuming that the other poses in L are correct. This procedure is repeated until no more updates can be made. Each update can be computed efficiently because it depends only on the partial contribution of the selected ligand's pose to the binding score:

$$\hat{\ell}_q = \underset{\ell_q}{\text{argmin}} \left[ (n-1)E^{dock}(\ell_q) + \sum_{i \neq q} -\log \frac{f(s(\ell_q, \ell_i); \text{Native})}{f(s(\ell_q, \ell_i), \text{Reference})} \right].$$

In order to account for the non-convex nature of the ComBind score, this algorithm was repeated from 500 initial configurations, explicitly including the initial configuration corresponding to the generic scoring function predictions at least once and return the best scoring configuration. Empirically this procedure converges to the same result over multiple runs.

DOCTRINE OF EQUIVALENTS

Having described several embodiments, it will be recognized by those skilled in the art that various modifications, alternative constructions, and equivalents may be used without departing from the spirit of the invention. Additionally, a number of well-known processes and elements have not been described in order to avoid unnecessarily obscuring the present invention. Accordingly, the above description should not be taken as limiting the scope of the invention.

Those skilled in the art will appreciate that the foregoing examples and descriptions of various preferred embodiments of the present invention are merely illustrative of the invention as a whole, and that variations in the components or steps of the present invention may be made within the spirit and scope of the invention. Accordingly, the present invention is not limited to the specific embodiments described herein, but, rather, is defined by the scope of the appended claims.

What is claimed is:

1. A method for predicting ligand-protein interaction comprising:
obtaining a set of ligands known to bind to a target protein;
generating a set of candidate poses for each ligand in the set of ligands and a candidate ligand; and
determining a pose for the candidate ligand based on a similarity of the candidate poses for the candidate ligand and the candidate poses for each ligand in the set of ligands;
wherein the similarity is based on pairwise comparisons between each ligand in the set of ligands and every other ligand in the set of ligands and pairwise comparisons between the candidate ligand and every ligand in the set of ligands.

2. The method of claim 1, wherein generating a set of candidate poses is accomplished by docking at least one ligand from the set of ligands using docking software.

3. The method of claim 1, wherein at least one ligand in the set of ligands has an experimentally determined pose; and wherein the pose for the at least one ligand is set to the experimentally determined pose.

4. The method of claim 1, wherein the similarity is further based on pairwise comparisons of substructures between each ligand in the set of ligands and every other ligand in the set of ligands and pairwise comparisons between the candidate ligand and every ligand in the set of ligands.

5. The method of claim 1, wherein the similarity is further based on pairwise comparisons of a protein-ligand interaction between each ligand in the set of ligands and every other ligand in the set of ligands and pairwise comparisons between the candidate ligand and every ligand in the set of ligands.

6. The method of claim 1, wherein determining a pose for the candidate ligand comprises determining a pose for each ligand in the set of ligands that minimizes the potential of all ligands.

7. The method of claim 6, wherein the potential is determined by:

$$E(L) = (n-1)E^{dock}(L) + E^{pairwise}(L),$$

where L=($\ell_1, \ldots, \ell_n$) indexes the candidate poses for each ligand, n is the number of ligands, $E^{dock}$ represents the standard docking scores for the set of ligand poses, and $E^{pairwise}$ represents a pairwise contribution to the total score.

8. The method of claim 7, wherein $E^{pairwise}((L)= \Sigma_{(i,j),i\neq j}e^{pairwise}(\ell_i, \ell_j)$.

9. A method for virtual screening, comprising:
obtaining a set of ligands known to bind to a target protein;
determining a pose for each ligand in the set of ligands by generating a set of candidate poses for ligands in the set of ligands, wherein the pose is based on a similarity of the candidate poses for each ligand in the set of ligands; and
determining a binding affinity of at least one candidate ligand by determining whether the candidate ligands binds to the target protein based on similarities to each ligand in the set of ligands and determining an energy if the candidate ligand binds to the target ligand;
wherein the similarity is based on pairwise comparisons between each ligand in the set of ligands and every other ligand in the set of ligands.

10. The method of claim 9, wherein determining a binding affinity of a candidate ligand determines a binding affinity of at least two candidate ligands; the method further comprising obtaining a library of candidate ligands, wherein determining a binding affinity of at least one candidate ligand determines a binding affinity of at least one candidate ligand in the library of candidate ligands.

11. The method of claim 9, further comprising fixing a pose for each ligand in the set of ligands prior to determining a binding affinity of at least one candidate ligand.

12. The method of claim 9, wherein the similarities are further based on pairwise comparisons of substructures between each ligand in the set of ligands and every other ligand in the set of ligands and pairwise comparisons between the candidate ligand and every ligand in the set of ligands.

13. The method of claim 9, wherein the similarities are further based on pairwise comparisons of a protein-ligand interaction between each ligand in the set of ligands and every other ligand in the set of ligands and pairwise comparisons between the candidate ligand and every ligand in the set of ligands.

14. The method of claim 9, wherein determining a pose for the candidate ligand comprises determining a pose for each ligand in the set of ligands that minimizes the potential of all ligands.

15. The method of claim 14 wherein the potential is determined by:

$$E(L) = (n-1)E^{dock}(L) + E^{pairwise}(L),$$

where L=($\ell_1, \ldots, \ell_n$) indexes the candidate poses for each ligand, n is the number of ligands, $E^{dock}$ represents the standard docking scores for the set of ligand poses, and $E^{pairwise}$ represents a pairwise contribution to the total score.

16. The method of claim 15, wherein $E^{pairwise}(L)= \Sigma_{(i,j),i\neq j}e^{pairwise}(\ell_i, \ell_j)$.

17. The method of claim 7, wherein $e^{pairwise}$ is determined using a machine learning algorithm, wherein the machine learning algorithm is fit to a benchmark set of pairs of correct poses and pairs of incorrect poses for a diverse set of proteins.

18. The method of claim 15, wherein $e^{pairwise}$ is determined using a machine learning algorithm, wherein the machine learning algorithm is fit to a benchmark set of pairs of correct poses and pairs of incorrect poses for a diverse set of proteins.

* * * * *